United States Patent
Grimm et al.

(10) Patent No.: US 6,872,245 B2
(45) Date of Patent: Mar. 29, 2005

(54) AZO PIGMENTS

(75) Inventors: Felix W. Grimm, Hofheim (DE); Hans Joachim Metz, Darmstadt (DE); Andreas Wacker, Lampertheim (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/486,072

(22) PCT Filed: Jul. 24, 2002

(86) PCT No.: PCT/EP02/08227

§ 371 (c)(1),
(2), (4) Date: Feb. 6, 2004

(87) PCT Pub. No.: WO03/014227

PCT Pub. Date: Feb. 20, 2003

(65) Prior Publication Data

US 2004/0231557 A1 Nov. 25, 2004

(30) Foreign Application Priority Data

Aug. 7, 2001 (DE) .......................... 101 38 770

(51) Int. Cl.$^7$ .................. C09B 29/20; C07D 239/96; C08K 5/3465; C09D 11/02
(52) U.S. Cl. .................. 106/496; 47/57.6; 106/31.77; 349/106; 430/7; 430/108.23; 524/92; 534/579; 534/801
(58) Field of Search .................. 106/31.77, 496; 430/7, 108.23; 349/106; 47/57.6; 524/92; 534/579, 801

(56) References Cited

U.S. PATENT DOCUMENTS

| 3,118,870 | A | * | 1/1964 | Dietz et al. | 534/801 |
|---|---|---|---|---|---|
| 3,897,411 | A | * | 7/1975 | Mory et al. | 534/742 |
| 4,052,377 | A | * | 10/1977 | Junge et al. | 534/798 |
| 4,229,344 | A | * | 10/1980 | Muller et al. | 534/731 |
| 4,247,296 | A | * | 1/1981 | Liedeck et al. | 8/506 |
| 4,392,999 | A | * | 7/1983 | Muller et al. | 534/801 |
| 4,997,920 | A | | 3/1991 | Hari et al. | 534/651 |
| 5,128,454 | A | * | 7/1992 | Frolich | 534/575 |
| 6,504,045 | B2 | * | 1/2003 | Jung et al. | 560/34 |
| 6,602,342 | B2 | * | 8/2003 | Schmidt et al. | 106/498 |
| 6,706,864 | B1 | * | 3/2004 | Vincent et al. | 534/774 |

FOREIGN PATENT DOCUMENTS

| DE | 1289928 | 2/1969 |
|---|---|---|
| EP | 0359708 | 3/1990 |
| GB | 1001706 | 8/1965 |

* cited by examiner

Primary Examiner—Anthony J. Green
(74) Attorney, Agent, or Firm—Anthony A. Bisulca

(57) ABSTRACT

This invention relates to azo pigments of general formula (I) wherein D represents the radical of a diazo component; $R^1$ and $R^2$ are the same or different and represent hydrogen, a $C_1$–$C_4$ alkyl radical which is optionally substituted by hydroxy, amino, halogen or methoxy, or a ($C_6$–$C_{10}$) aryl radical which is optionally substituted by one, two or three substituents from the group $C_1$–$C_4$ alkyl, $C_1$–$C_4$ alkoxy, F, Cl, Br, $CF_3$, $NO_2$, OH, $CONH_2$, $CONH(C_1$–$C_4$ alkyl), $CON(C_1$–$C_4$ alkyl)$_2$, $COO(C_1$–$C_4$ alkyl), $SO_2NH_2$, $SO_2NH$ ($C_1$–$C_4$ alkyl) and $SO_2N(C_1$–$C_4$ alkyl)$_2$, provided that $R^1$ and $R^2$ do not simultaneously represent hydrogen; $R^4$ represents hydrogen, $C_1$–$C_4$ alkyl, halogen, trifluoromethyl, $C_1$–$C_4$ alkoxy, $NO_2$, or CN; and n represents 1, 2 or 3

(I)

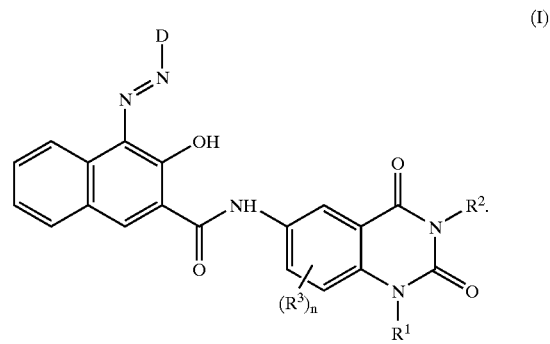

11 Claims, No Drawings

AZO PIGMENTS

The present invention relates to novel azo pigments constructed on N-substituted 6-(2'-hydroxy-3'-naphthoylamino)quinazoline-2,4-dione coupling components.

Azo pigments of the 2-hydroxy-3-naphthoanilides, such as C.I. Pigment Red 2, 9, 12, 14, 112, 144, 146, 147, 170, 175, 184, 185, 187, 188, 210, 247 or 256, for example, possess great importance for the coloring of high molecular mass organic materials. A disadvantage of these pigments is their light fastness and weather fastness in challenging applications, which are no longer up to present-day requirements.

Likewise known are coupling components obtained by condensing 2-hydroxy-3-naphtholic acid with 6-aminoquinazoline-2,4-dione (DE-A-12 89 928). The colorants produced therewith, however, feature cloudy, fairly dull shades and unfavorable rheological properties, disperse poorly in the application medium, and are weak in color.

It was an object of the present invention to provide novel pigments featuring high light and weather fastness and also brilliant shades, which additionally process well in the application medium.

It has now been found that compounds of the general formula (I) defined below surprisingly meet these requirements.

The present invention provides azo pigments of the formula (I)

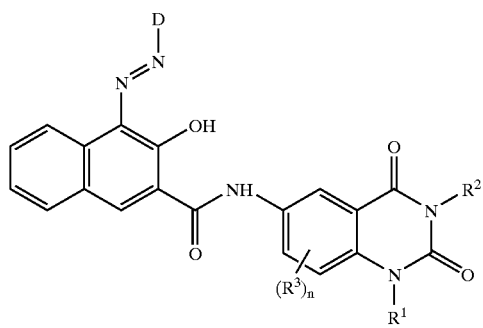

(I)

in which D is the radical of a diazo component, $R^1$ and $R^2$ are identical or different and are hydrogen, an optionally hydroxy-, amino-, halo- or methoxy-substituted $C_1$–$C_4$-alkyl radical, or a ($C_6$–$C_{10}$)-aryl radical which is unsubstituted or substituted by 1, 2 or 3 substituents from the group consisting of $C_1$–$C_4$-alkyl, $C_1$–$C_4$-alkoxy, F, Cl, Br, $CF_3$, $NO_2$, OH, $CONH_2$, $CONH(C_1$–$C_4$-alkyl), $CON(C_1$–$C_4$-alkyl)$_2$, COO ($C_1$–$C_4$-alkyl), $SO_2NH_2$, $SO_2NH(C_1$–$C_4$-alkyl) and $SO_2N(C_1$–$C_4$-alkyl)$_2$, with the proviso that $R^1$ and $R^2$ are not simultaneously hydrogen;

$R^3$ is hydrogen, $C_1$–$C_4$-alkyl, halo, especially fluoro, chloro or bromo, trifluoromethyl, $C_1$–$C_4$-alkoxy, $NO_2$, or CN, and n is 1, 2 or 3.

The general formula (I) is to be understood as an idealized representation and also embraces the corresponding tautomeric compounds, and also the possible configurational isomers of each tautomeric form.

Preferred radicals $R^1$ and $R^2$ are hydrogen, methyl, ethyl or phenyl, with the aforementioned proviso.

Particularly preferred azo pigments are those wherein $R^1$ is methyl or ethyl and $R^2$ is hydrogen.

Preferred radicals $R^3$ are hydrogen, methyl, ethyl, methoxy, ethoxy, F, Cl, $CF_3$ and nitro.

Preferred radicals D are ($C_6$–$C_{12}$)-aryl radicals substituted by 1, 2 or 3 substituents from the group consisting of $C_1$–$C_4$-alkyl, $C_1$–$C_4$-alkoxy, phenyl, chlorophenyl, dichlorophenyl, F, Cl, Br, $CF_3$, $NO_2$, $NH_2$, COOH, OH, $CONH_2$, $CONH(C_1$–$C_4$-alkyl), $CON(C_1$–$C_4$-alkyl)$_2$, COO ($C_1$–$C_4$-alkyl), $SO_2NH_2$, $SO_2NH(C_1$–$C_4$-alkyl) and $SO_2N(C_1$–$C_4$-alkyl)$_2$, or a ($C_6$–$C_{10}$)-aryl radical to which a five- or six-membered heterocyclic ring having 1, 2 or 3 heteroatoms from the group consisting of N, O and S is fused.

The present invention also provides a process for preparing the compounds of the formula (I), which comprises diazotizing an aromatic amine of the formula D-$NH_2$ and coupling the product with one or more compounds of the formula (II),

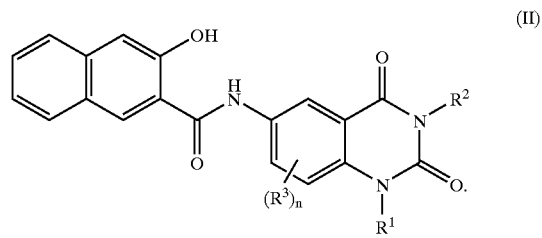

(II)

Particularly preferred aromatic amines D-$NH_2$ are: 2-chloroaniline, 4-methyl-2-nitroaniline, 4-chloro-2-nitroaniline, 3,3'-dichlorobiphenyl-4,4'-diamine, 3,3'-dimethylbiphenyl-4,4'-diamine, 4-methoxy-2-nitroaniline, 2-methoxy-4-nitroaniline, 4-nitroaniline, dimethyl 5-aminoisophthalate, methyl anthranilate, 2-trifluoromethyl-aniline, dimethyl 2-amino-terephthalate, 2-methoxyaniline, 2,4-dinitroaniline, 3-amino-4-chlorobenzamide, 3-amino-4-methylbenzamide, 2,5-dichloroaniline, 2-chloro-4-nitroaniline, 2-methyl-5-nitroaniline, 2-methyl-4-nitroaniline, 2,4,5-trichloroaniline, 4-aminobenzamide, 4-amino-5-methoxy-N,N-dimethylbenzenesulfonamide, monomethyl 2-amino-N-(2,5-dichlorophenyl)terephthalate, butyl 2-aminobenzoate, 2-chloro-5-trifluoromethylaniline, 4-amino-2,5-dichloro-N-methylbenzenesulfonamide, 4-amino-2,5-dichloro-N,N-dimethylbenzenesulfonamide, 6-amino-1H-quinazoline-2,4-dion, 4-amino-2,5-dimethoxy-N-methylbenzenesulfonamide, 2,4-dichloroaniline, 5-chloro-2-methylaniline, 2-aminobenzoic acid, 3-amino-4-methoxy-N-phenylbenzamide, 3-amino-N-[4-(aminocarbonyl)phenyl]-4-methoxybenzamide, 4-amino-5-methoxy-2-methyl-N-methylbenzolsulfonamide, 5-amino-benzimidazol-2-on, 6-amino-quinoxaline-2,3-dion, 6-methoxy-7-aminoquinoxaline-2,3-dion, 4-amino-2,5-dimethoxy-N-phenylbenzolsulfonamide, 4-amino-N-[4-(aminocarbonyl) phenyl]benzamide, 1,2-bis-(2-aminophenoxy)ethane, 2-ethoxyaniline and 4-ethoxyaniline.

The temperatures of the azo coupling are normally from −10 to +90° C., preferably from −5 to +80° C., in particular from 0 to 70° C. The azo coupling reaction takes place preferably in aqueous solution or suspension, although organic solvents, alone or in a mixture with water, can also be used, examples being alcohols having 1 to 10 carbon atoms, such as methanol, ethanol, n-propanol, isopropanol, butanols, such as n-butanol, sec-butanol, tert-butanol, pentanols, such as n-pentanol, 2-methyl-2-butanol, hexanols, such as 2-methyl-2-pentanol, 3-methyl-3- pentanol, 2-methyl-2-hexanol, 3-ethyl-3-pentanol, octanols, such as 2,4,4-trimethyl-2-pentanol, cyclohexanol; or glycols, such as ethylene glycol, diethylene glycol, propylene glycol, dipropylene glycol, or glycerol; polyglycols, such as polyethylene glycols or polypropylene glycols; ethers, such as methyl isobutyl ether, tetrahydrofuran or dimethoxyethane; glycol ethers, such monomethyl or monoethyl ethers of ethylene glycol or of propylene glycol, diethylene glycol monomethyl ether, diethylene glycol monoethyl ether, butyl glycols or methoxybutanol; ketones, such as acetone, diethyl ketone, methyl isobutyl ketone, methyl ethyl ketone or cyclohexanone; aliphatic acid amides, such as formamide, dimethylformamide, N-methylacetamide or N,N-dimethylacetamide; urea derivatives, such as tetramethylurea; or cyclic carboxyamides, such as N-methylpyrrolidone, valerolactam or caprolactam; esters, such as $C_1$–$C_6$-alkyl carboxylates, such as butyl formate, ethyl acetate or propyl propanoate; or carboxylic acid $C_1$–$C_6$-glycol esters; or glycol ether acetates, such as 1-methoxy-2-propyl acetate; or $C_1$–$C_6$-alkyl phthalates or benzoates such as ethyl benzoate; cyclic esters, such as caprolactone; nitriles, such as acetonitrile or benzonitrile; aliphatic or aromatic hydrocarbons, such as cyclohexane or benzene; or alkyl-, alkoxy-, nitro- or halo-substituted benzene, such as toluene, xylene, ethylbenzene, anisole, nitrobenzene, chlorobenzene, o-dichlorobenzene, 1,2,4-trichlorobenzene or bromobenzene; or other substituted aromatics, such as benzoic acid or phenol; aromatic heterocycles, such as pyridine, morpholine, picoline or quinoline; and also hexamethylphosphoramide, 1,3-dimethyl-2-imidazolidinon, dimethyl sulfoxide and sulfolane. Said solvents can also be used as mixtures. Preference is given to using water-miscible solvents.

In the process of the invention it is also possible to employ customary auxiliaries such as, for example, coupling assistants, surfactants, pigmentary and non-pigmentary dispersants, fillers, standardizers, resins, waxes, defoamers, antidust agents, extenders, shading colorants, preservatives, drying retardants, rheology control additives, wetting agents, antioxidants, UV absorbers, light stabilizers, or a combination thereof.

The total amount of assistants added can amount to from 0 to 40% by weight, preferably from 1 to 30% by weight, more preferably from 2.5 to 25% by weight, based on the azo pigment.

Suitable surfactants include anionic or anion-active, cationic or cation-active, and nonionic substances, or mixtures of these agents.

Examples of suitable anionic substances include fatty acid taurides, fatty acid N-methyltaurides, fatty acid isethionates, alkylphenylsulfonates, alkylnaphthalenesulfonates, alkylphenol polyglycol ether sulfates, fatty alcohol polyglycol ether sulfate, fatty acid amide polyglycol ether sulfates, alkylsulfosuccinamates, alkenylsuccinic monoesters, fatty alcohol polygylcol ether sulfosuccinates, alkanesulfonates, fatty acid glutamates, alkylsulfosuccinates, fatty acid sarcosides; fatty acids, examples being palmitic, stearic and oleic acid; soaps, examples being alkali metal salts of fatty acids, naphthenic acids and resin acids, such as abietic acid, alkali-soluble resins, examples being rosin-modified maleate resins and condensation products based on cyanuric chloride, taurine, N,N'-diethylaminopropylamine and p-phenylenediamine. Particular preference is given to resin soaps, i.e., alkali metal salts of resin acids.

Examples of suitable cationic substances include quaternary ammonium salts, fatty amine alkoxylates, alkoxylated polyamines, fatty amine polyglycol ethers, fatty amines, diamines and polyamines derived from fatty amines or fatty alcohols, and the alkoxylates of said amines, imidazolines derived from fatty acids, and salts of these cationic substances, such as acetates, for example.

Examples of suitable nonionic substances include amine oxides, fatty alcohol polyglycol ethers, fatty acid polyglycol esters, betaines, such as fatty acid amide N-propyl betaines, phosphoric esters of aliphatic and aromatic alcohols, fatty alcohols or fatty alcohol polyglycol ethers, fatty acid amine ethoxylates, fatty alcohol-alkylene oxide adducts, and alkylphenol polyglycol ethers.

By non-pigmentary dispersants are meant substances which in structural terms are not derived from organic pigments by chemical modification. There are added as dispersants either during the actual preparation of pigments or else in many cases during the incorporation of the pigments into the application media to be colored: for example, during the preparation of paints or printing inks by dispersing of the pigments into the corresponding binders. They may be polymeric substances, such as polyolefins, polyesters, polyethers, polyamides, polyimines, polyacrylates, polyisocyanates, block copolymers thereof, copolymers of the corresponding monomers, or polymers of one class modified with a few monomers from another class. These polymeric substances carry polar anchor groups such as hydroxyl, amino, imino, and ammonium groups, carboxylic acid and carboxylate groups, sulfonic acid and sulfonate groups or phosphonic acid and phosphonate groups, for example, and can also be modified with aromatic, non-pigmentary substances. Non-pigmentary dispersants may additionally be aromatic substances modified chemically with functional groups but not derived from organic pigments. Non-pigmentary dispersants of this kind are known to the skilled worker and in some cases are available commercially (e.g., Solsperse®, Avecia; Disperbyk®, Byk, Efka®, Efka). A number of types will be mentioned below as representatives; however, it is possible in principle to use any desired other substances described, examples being condensation products of isocyanates and alcohols, diols or polyols, amino alcohols or diamines or polyamines, polymers of hydroxycarboxylic acids, copolymers of olefinic monomers or vinyl monomers and ethylenically unsaturated carboxylic esters, urethane-containing polymers of ethenically unsaturated monomers, urethane-modified polyesters, condensation products based on cyanuric halides, polymers containing nitroxyl compounds, polyesteramides, modified polyamides, modified acrylic polymers, comb dispersants comprising polyesters and acrylic polymers, phosphoric esters, triazine-derived polymers, modified polyethers, or dispersants derived from aromatic, non-pigmentary substances. These base structures are in many cases modified further, by means for example of chemical reaction with further substances which carry functional groups, or by formation of salts.

By pigmentary dispersants are meant pigment dispersants which derive from an organic pigment base structure and are prepared by chemical modification of said base structure; examples include pigment dispersants containing saccharin, piperidyl-containing pigment dispersants, naphthalene- or perylene-derived pigment dispersants, pigment dispersants containing functional groups linked to the pigment base structure via a methylene group, pigment base structures modified chemically with polymers, pigment dispersants containing sulfo acid groups, pigment dispersants containing sulfonamide groups, pigment dispersants containing ether groups, or pigment dispersants containing carboxylic acid, carboxylic ester or carboxamide groups.

In order to set a desired pH it is possible to supply buffer solutions, preferably of organic acids and their salts, such as formic acid/formate buffer, acetic acid/acetate buffer, and citric acid/citrate buffer, for example; or of inorganic acids and their salts, such as phosphoric acid/phosphate buffer or carbonic acid/hydrogen carbonate or carbonate buffer, for example.

The azo pigment is preferably isolated immediately after the reaction. An alternative option is to carry out an after-treatment (finish) with water and/or an organic solvent, at temperatures for example of from 20 to 250° C., where appropriate with the addition of assistants. For this purpose, for example, it is possible to heat the moist or dried pigments in water or in organic solvents, such as pyridine, N-methyl-2-pyrrolidone, dimethylformamide, dimethylacetamide, dimethyl sulfoxide, alcohols, chlorobenzenes, glacial acetic acid, quinoline or glycols, for example, or in a mixture of these solvents, for a certain time, where appropriate under increased pressure and where appropriate with addition of nonionic or ionic surface-active substances.

The present invention additionally provides the coupling components of the general formula (II),

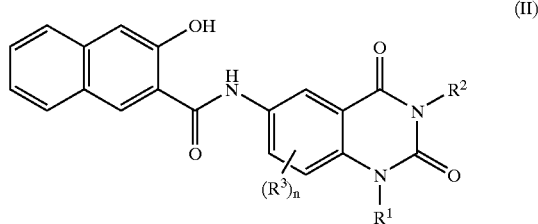

(II)

in which $R^1$, $R^2$ and $R^3$ are as defined above, and also the corresponding tautomeric forms and the respective configurational isomers of each tautomeric form.

The compounds of the formula (II) can be prepared by condensing 2-hydroxy-3-naphthoic acid or 2-hydroxy-3-naphthoyl chloride with an amine of the general formula (IV), preferably at temperatures between 0 and 80° C. and in the presence of $PCl_3$ and a base, such as pyridine.

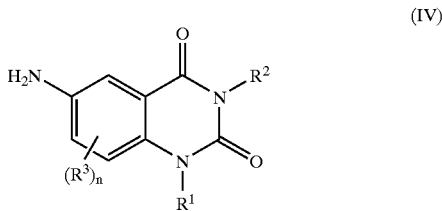

(IV)

The compounds of the formula (I) according to the invention are particularly suitable for pigmenting varnishes, plastics, printing inks, electrophotographic toners and developers, powder coating materials, graphics inks, preferably ink-jet inks, aqueous and nonaqueous pigment preparations, and color filters, and also for coloring seed.

By way of example it is possible to pigment natural or synthetic organic materials of high molecular mass, such as cellulose ethers and cellulose esters, such as ethylcellulose, nitrocellulose, cellulose acetate or cellulose butyrate, natural resins or synthetic resins, such as addition-polymerization resins or condensation resins, examples being amino resins, especially urea-formaldehyde and melamine-formaldehyde resins, alkyd resins, acrylic resins, phenolic resins, polycarbonates, polyolefins, such as polystyrene, polyvinyl chloride, polyethylene, polypropylene, polyacrylonitrile, polyacrylic esters, polyamides, polyurethane or polyesters, rubber, latices, casein, silicones and silicone resins, for example, individually or in mixtures.

It is irrelevant whether the aforementioned organic compounds of high molecular mass are in the form of plastic masses, casting resins, pastes, melts or in the form of spinning solutions, varnishes, stains, foams, watercolors, graphics inks, dressings, coating materials, emulsion paints or printing inks. Depending on the intended use it is found advantageous to utilize the azo colorants of the invention in the form of blends or else as preparations or dispersions. Based on the high molecular mass organic material for coloring, the azo colorants prepared in accordance with the invention are used in an amount of preferably from 0.05 to 30% by weight, more preferably from 0.1 to 15% by weight.

The azo pigments of the invention can be used, for example, to pigment the industrially common baking varnishes from the class of the alkyd-melamine resin varnishes, acrylic-melamine resin varnishes, polyester varnishes, high-solids acrylic resin varnishes, aqueous, polyurethane-based varnishes, and two-component varnishes based on polyisocyanate-crosslinkable acrylic resins, and especially automotive metallic paints.

The azo colorants of the invention are also suitable for use as colorants in electrophotographic toners and developers, such as one- or two-component powder toners (also called one- or two-component developers), magnetic toners, liquid toners, polymerization toners, and specialty toners, for example.

Typical toner binders are addition-polymerization, polyaddition, and polycondensation resins, such as styrene, styrene-acrylate, styrene-butadiene, acrylic, polyester, phenol-epoxy resins, polysulfones, polyurethanes, individually or in combination, and also polyethylene and polypropylene, which may also already include, or be modified subsequently with, further ingredient additions, such as charge control agents, waxes or flow assistants.

The azo colorants of the invention are further suited to use as colorants in powders and powder coating materials, particularly in triboelectrically or electrokinetically sprayable powder coating materials which are employed to coat the surfaces of articles made, for example, from metal, wood, plastic, glass, ceramic, concrete, textile material, paper or rubber. Resins used as powder coating resins are typically epoxy resins, carboxyl- and hydroxyl-containing polyester resins, polyurethane resins, and acrylic resins, together with customary curatives. Resin combinations also find use. Thus, for example, epoxy resins are frequently employed in combination with carboxyl- and hydroxyl-containing polyester resins.

Typical curative components (depending on the resin system) are, for example, acid anhydrides, imidazoles, and also dicyandiamide and its derivatives, blocked isocyanates, bisacylurethanes, phenolic resins and melamine resins, triglycidyl isocyanurates, oxazolines, and dicarboxylic acids.

The azo colorants of the invention are additionally suitable for use as colorants in ink-jet inks, on both an aqueous and a nonaqueous basis, and also in those inks which operate in accordance with the hot-melt process.

Furthermore, the azo colorants of the invention are suitable, too, as colorants for color filters, and also for both subtractive and additive color generation.

For the stated applications the compounds of the formula (I) can be used as powders, presscakes or flush pastes.

The compounds of the formula (I) according to the invention feature bright shades, high light fastness, solvent fastness and fastness to overcoating, temperature stability, high color strengths, effective dispersibility in the application medium, and good rheological properties.

From among the multiplicity of known varnishes, an aromatics-containing alkyd-melamine (AM) varnish based on a medium-oil, nondrying alkyd resin was selected in order to assess the properties of the pigments prepared in accordance with the invention in the coatings sector.

In the examples below, parts and percentages are by weight.

Preparation of 1-methyl-6-(2'-hydroxy-3'-naphthoylamino)quinazoline-2,4-dione 50 parts of 2-hydroxy-3-naphtholic acid and 51.6 parts of 6-amino-1-methylquinazoline-2,4-dione are suspended in 200 parts of pyridine and at 30 to 50° C. 20.4 parts of phosphorus trichloride are added dropwise over the course of 30 minutes. The mixture is subsequently stirred at 100° C. for 1 hour, 300 parts of water are added, and the pyridine is expelled using steam. After cooling to room temperature the mixture is filtered with suction and the filter product is washed with water and dried. This gives 67 parts of an ocher-colored solid.

EXAMPLE 1

9.7 parts of butyl anthranilate are diazotized in 50 parts of water and 17.3 parts of 31% strength hydrochloric acid with 8.8 parts of 40% strength sodium nitrite solution at from 5 to 10° C., the product is diluted with 200 parts of water and clarified, and the nitrite excess is eliminated. Then the diazonium salt solution is admixed with 10 parts of a 10% strength solution of ®Genapol T250 in water and 200 parts of a 4-molar sodium acetate solution. 18.97 parts of 1-methyl-6-(2'-hydroxy-3'-naphthoylamino)quinazoline-2,4-dione are dissolved in 600 parts of water and 20.4 parts of 33% strength sodium hydroxide solution. The coupler solution thus prepared is metered into the diazonium salt solution over the course of 25 minutes. Thereafter the mixture is stirred at a pH of 6.2 and at 30° C. until diazonium salt is no longer detectable, and is then stirred at 94° C. for 30 minutes more, and filtered, and the product is washed with water. The moist presscake is suspended in 855 parts of dimethylformamide and stirred at 100° C. for aftertreatment. The suspension is subsequently filtered and the solid product is washed, dried, and ground. This gives 21.0 parts of red pigment.

EXAMPLE 2

6.8 parts of p-aminobenzamide are dissolved in 50 parts of water and 17.3 parts of 31% strength hydrochloric acid and diazotized with 8.8 parts of 40% strength sodium nitrite solution at from 0 to 5° C., the product mixture is diluted with 200 parts of water, and the nitrite excess is eliminated. The diazonium salt solution is then admixed with 10 parts of a 10% strength solution of ®Genapol T250 in water and 200 parts of a 4-molar sodium acetate solution.

18.97 parts of 1-methyl-6-(2'-hydroxy-3'-naphthoylamino)quinazoline-2,4-dione are dissolved in 600 parts of water and 20.4 parts of 33% strength sodium hydroxide solution. The coupler solution thus prepared is metered into the diazonium salt solution over the course of 25 minutes. The mixture is subsequently stirred at a pH of from 5.5 to 6.0 until diazonium salt is no longer detectable, when it is stirred at 94° C. for 30 minutes more and filtered, and the solid product is washed with water and dried. The dried crude pigment is ground and for the purpose of aftertreatment is suspended in 500 parts of N-methylpyrrolidone and stirred at 106° C. for 25 minutes. It is subsequently filtered, washed, dried, and ground. This gives 17.4 parts of a red pigment.

EXAMPLE 3

11.5 parts of 4-amino-5-methoxy-2-methylbenzene-N-methylsulfonamide are dissolved in 50 parts of water and 17.3 parts of 31% strength hydrochloric acid and diazotized with 8.8 parts of 40% strength sodium nitrite solution at from 0 to 5° C., the mixture is diluted with 200 parts of water, and the nitrite excess is eliminated. The diazonium salt solution is then admixed with 10 parts of a 10% strength solution of ®Genapol T250 in water and 200 parts of a 4-molar sodium acetate solution. 18.97 parts of 1-methyl-6-(2'-hydroxy-3'-naphthoylamino)quinazoline-2,4-dione are dissolved in 600 parts of water and 20.4 parts of 33% strength sodium hydroxide solution. The coupler solution thus prepared is metered into the diazonium salt solution over the course of 25 minutes. The mixture is subsequently stirred at a pH of from 5.5 to 6.0 until diazonium salt is no longer detectable, when it is stirred at 94° C. for 30 minutes more and filtered, and the solid product is washed with water. The moist presscake is suspended in 700 parts of acetic acid and for aftertreatment is stirred at 100° C. It is subsequently filtered, washed, dried, and ground. This gives 27.6 parts of a red pigment.

The procedure of example 1 is repeated, using as coupling component the above-prepared 1-methyl-6-(2'-hydroxy-3'-naphthoylamino)quinazoline-2,4-dione and also the diazo components listed in table 1:

TABLE 1

| Example | Diazo component | Shade |
|---|---|---|
| 1 | 2-aminobenzoic acid butyl ester ($NH_2$, $C(O)O$-butyl on benzene) | red/yellowish |
| 2 | 4-aminobenzamide ($NH_2$-C$_6$H$_4$-C(O)NH$_2$) | red/neutral |
| 3 | 4-amino-5-methoxy-2-methylbenzene-N-methylsulfonamide ($NH_2$, OMe, Me, $SO_2NHCH_3$ on benzene) | red/neutral |
| 4 | 2-aminobenzoic acid methyl ester ($NH_2$, $C(O)OCH_3$ on benzene) | red/neutral |

TABLE 1-continued

| Example | Diazo component | Shade |
|---|---|---|
| 5 | (2-methoxy-4-nitroaniline) | red/bluish |
| 6 | (3-amino-4-methylbenzamide) | red/yellowish |
| 7 | (3-amino-4-chlorobenzamide) | red/neutral |
| 8 | (methyl 2-amino-4-carbamoylbenzoate) | red/yellowish |
| 9 | (2-chloro-4-trifluoromethylaniline) | red/neutral |
| 10 | (3-amino-4-methoxybenzamide) | red/neutral |

COMPARATIVE EXAMPLE 1

For the preparation of the pigment the procedure described in example 2 is repeated but using 6-(2'-hydroxy-3'-naphthoylamino)quinazoline-2,4-dione instead of the 1-methyl-6-(2'-hydroxy-3'-naphthoylamino)quinazoline-2,4-dione. This gives 28.1 g of a red pigment

COMPARATIVE EXAMPLE 2

For the preparation of the pigment the procedure described in example 3 is repeated but using 6-(2'-hydroxy-3'-naphthoylamino)quinazoline-2,4-dione instead of the 1-methyl-6-(2'-hydroxy-3'-naphthoylamino)quinazoline-2,4-dione. This gives 28.5 g of a red pigment.

To assess the performance properties of the pigments of the invention an alkyd-melamine (AM) varnish system was selected. In relation to the comparative examples the pigments of the invention are distinguished by significantly higher color strengths, purer hues, and significantly higher hiding power.

Example 2 in comparison to comparative example 1:

| Color strength: | 195% |
|---|---|
| Purity difference (chroma): | dC = 3.49 |

Example 3 in comparison to comparative example 2:

| Color strength: | 115% |
|---|---|
| Purity difference (chroma): | dC = 5.52 |

What is claimed is:
1. An azo pigment of the formula (I),

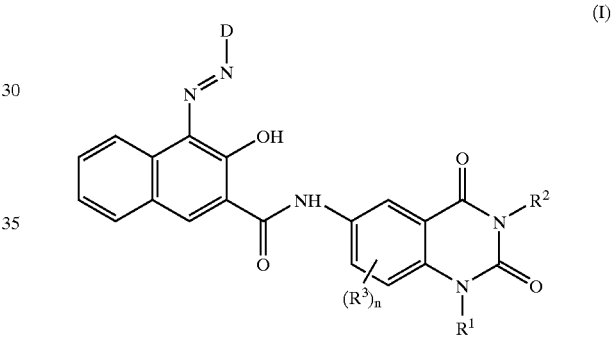

in which D is the radical of a diazo component,
$R^1$ and $R^2$ are identical or different and are hydrogen, $C_1$–$C_4$-alkyl radical, or a ($C_6$–$C_{10}$)-aryl radical which is unsubstituted or substituted by 1, 2 or 3 substituents selected from the group consisting of $C_1$–$C_4$-alkyl, $C_1$–$C_4$-alkoxy, F, Cl, Br, $CF_3$, $NO_2$, OH, $CONH_2$, $CONH(C_1$–$C_4$-alkyl), $CON(C_1$–$C_4$-alkyl)$_2$, COO ($C_1$–$C_4$-alkyl), $SO_2NH_2$, $SO_2NH(C_1$–$C_4$-alkyl) and $SO_2N(C_1$–$C_4$-alkyl)$_2$,
with the proviso that $R^1$ and $R^2$ are not simultaneously hydrogen:
$R^3$ is hydrogen, $C_1$–$C_4$-alkyl, halo, trifluoromethyl, $C_1$–$C_4$-alkoxy, $NO_2$, or CN, and
n is 1, 2 or 3.
2. An azo pigment as claimed in claim 1, wherein $R^1$ and $R^2$ are hydrogen, methyl, ethyl or phenyl.
3. An azo pigment as claimed in claim 1, wherein $R^1$ is methyl or ethyl and $R^2$ is hydrogen.
4. An azo pigment as claimed in claim 1, wherein $R^3$ is hydrogen, methyl, ethyl, methoxy, ethoxy, F, Cl, $CF_3$ or nitro.
5. An azo pigment as claimed in claim 1, wherein D is a ($C_6$–$C_{12}$)-aryl radical substituted by 1, 2 or 3 substituents selected from the group consisting of $C_1$–$C_4$-alkyl, $C_1$–$C_4$-alkoxy, phenyl, chlorophenyl, dichlorophenyl, F, Cl, Br, $CF_3$, $NO_2$, $NH_2$, COOH, OH, $CONH_2$, $CONH(C_1$–$C_4$- alkyl), CON($C_1$–$C_4$-alkyl)$_2$, COO($C_1$–$C_4$-alkyl), SO$_2$NH$_2$, SO$_2$NH($C_1$–$C_4$-alkyl), and SO$_2$N($C_1$–$C_4$-alkyl)$_2$ and a ($C_6$–$C_{10}$)-aryl radical, to which a five- or six-membered heterocyclic ring having 1, 2 or 3 heteroatoms selected from the group consisting of N, O and S is fused.

6. An azo pigment as claimed in claim 1, wherein the $C_1$–$C_4$-alkyl radical is hydroxy, amino, halogen or methoxy substituted.

7. A process for preparing an azo pigment as claimed in claim 1, comprising the steps of diazotizing an amine of formula D-NH$_2$ and coupling the product with a compound of the formula (II)

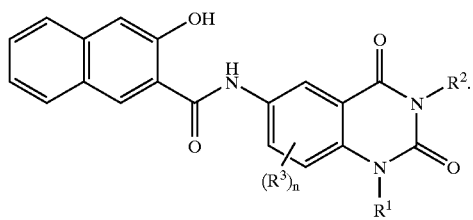

(II)

8. A composition comprising an azo pigment as claimed in claim 1, wherein the composition is selected from the group consisting of varnishes, plastics, printing inks, electrophotographic toners, electrophotographic developers, powder coating materials, graphics inks, ink-jet inks, aqueous and nonaqueous pigment preparations, and color filters.

9. A colored seed comprising an azo pigment as claimed in claim 1.

10. A compound of the formula (II)

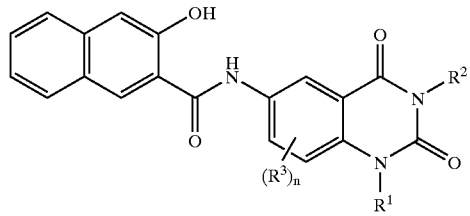

(II)

in which

R$^1$ and R$^2$ are identical or different and are hydrogen, $C_1$–$C_4$-alkyl radical, or a ($C_6$–$C_{10}$)-aryl radical which is unsubstituted or substituted by 1, 2 or 3 substituents selected from the group consisting of $C_1$–$C_4$-alkyl, $C_1$–$C_4$-alkoxy, F, Cl, Br, CF$_3$, NO$_2$, OH, CONH$_2$, CONH($C_1$–$C_4$-alkyl), CON($C_1$–$C_4$-alkyl)$_2$, COO ($C_1$–$C_4$-alkyl), SO$_2$NH$_2$, SO$_2$NH($C_1$–$C_4$-alkyl) and SO$_2$N($C_1$–$C_4$-alkyl)$_2$, with the proviso that R$^1$ and R$^2$ are not simultaneously hydrogen;

R$^3$ is hydrogen, $C_1$–$C_4$-alkyl, halo, trifluoromethyl, $C_1$–$C_4$-alkoxy, NO$_2$, or CN, and n is 1, 2 or 3.

11. The compound as claim in claim 10, wherein the $C_1$–$C_4$-alkyl radical is hydroxy, amino, halogen or methoxy substituted.

* * * * *